US011872079B2

(12) United States Patent
Duan et al.

(10) Patent No.: US 11,872,079 B2
(45) Date of Patent: Jan. 16, 2024

(54) ULTRASOUND SCANNING CONTROL METHOD, ULTRASOUND SCANNING DEVICE, AND STORAGE MEDIUM

(71) Applicant: KUNSHAN IMAGENE MEDICAL Co., Ltd., Kunshan (CN)

(72) Inventors: Bin Duan, Shenzhen (CN); Jin-Fu Li, Shenzhen (CN); Lin-Fei Xiong, Shenzhen (CN); Shu-Jian Hu, Shenzhen (CN); Yu-Jiao Wang, Shenzhen (CN); Shui-Fan Li, Shenzhen (CN)

(73) Assignee: KUNSHAN IMAGENE MEDICAL Co., Ltd., Kunshan (CN)

( * ) Notice: Subject to any disclaimer, the term of this patent is extended or adjusted under 35 U.S.C. 154(b) by 238 days.

(21) Appl. No.: 17/419,838

(22) PCT Filed: Jan. 29, 2019

(86) PCT No.: PCT/CN2019/073776
§ 371 (c)(1),
(2) Date: Jun. 30, 2021

(87) PCT Pub. No.: WO2020/154921
PCT Pub. Date: Aug. 6, 2020

(65) Prior Publication Data
US 2022/0079556 A1 Mar. 17, 2022

(51) Int. Cl.
*A61B 8/00* (2006.01)
(52) U.S. Cl.
CPC .......... *A61B 8/4218* (2013.01); *A61B 8/4245* (2013.01); *A61B 8/54* (2013.01)

(58) Field of Classification Search
CPC ....... A61B 8/4218; A61B 8/4245; A61B 8/54; A61B 8/429; A61B 8/4405
See application file for complete search history.

(56) References Cited

U.S. PATENT DOCUMENTS

| 8,024,071 | B2 * | 9/2011 | Komatsu | B25J 9/1682 |
| | | | | 318/568.22 |
| 10,335,116 | B2 * | 7/2019 | Boctor | A61B 34/30 |
| 2008/0021317 | A1 * | 1/2008 | Sumanaweera | A61B 8/4281 |
| | | | | 600/437 |

(Continued)

FOREIGN PATENT DOCUMENTS

| CN | 106562805 A | 4/2017 | |
| WO | WO-2019103053 A1 * | 5/2019 | A61B 34/37 |

*Primary Examiner* — Baisakhi Roy
*Assistant Examiner* — Kaitlyn E Sebastian
(74) *Attorney, Agent, or Firm* — ScienBiziP, P.C.

(57) ABSTRACT

An ultrasound scanning control method applied to an ultrasound scanning device is provided. The ultrasound scanning device includes an execution mechanism. The execution mechanism includes a mechanical arm and a probe. The ultrasound scanning control method includes: controlling the mechanical arm to drive the probe to move according to a set scanning trajectory; and controlling the probe to collect an ultrasound image. A target region is identified from the collected ultrasound image. The scanning trajectory is adjusted when a position of the target region in the ultrasound image is not a predetermined position, and the mechanical arm is controlled to drive the probe to move according to the adjusted scanning trajectory.

18 Claims, 5 Drawing Sheets

(56) References Cited

U.S. PATENT DOCUMENTS

2015/0272546 A1* 10/2015 Cheon ................... G16H 50/30
    600/440
2017/0143303 A1* 5/2017 Chen ...................... A61B 8/488
2017/0360401 A1* 12/2017 Rothberg ............. G06V 10/454

* cited by examiner

ULTRASOUND SCANNING CONTROL METHOD, ULTRASOUND SCANNING DEVICE, AND STORAGE MEDIUM

FIELD

The subject matter relates to a field of image processing technology, and more particularly, to an ultrasound scanning control method, an ultrasound scanning control system, an ultrasound scanning device, and a storage medium.

BACKGROUND

An existing ultrasound scanning device is semi-automatic and can only scan for a specific part, and an assistance of a nurse is required during a scanning process of the ultrasound scanning device. In addition, during an examination, an interaction between the ultrasound scanning device and people when the ultrasound scanning device is moving is rarely considered. The current technology does not have a good solution to enable the ultrasound scanning device to perform a prescribed action and keep flexible interaction with people.

SUMMARY

Thus, it is necessary to provide an ultrasound scanning control method, an ultrasound scanning control system, an ultrasound scanning device, and a storage medium, which can realize automatic scanning of the ultrasound scanning device and can realize flexible interaction between the ultrasound scanning device and a patient.

A first aspect of the present disclosure provides an ultrasound scanning control method applied to an ultrasound scanning device which including an execution mechanism, the execution mechanism including a mechanical arm and a probe, the ultrasound scanning control method including: controlling the mechanical arm to drive the probe to move based on a set scanning trajectory; controlling the probe to collect an ultrasound image; identifying a target area from the ultrasound image; calculating a position of the target area in the ultrasound image, and determining whether the position of the target area in the ultrasound image belongs to a predetermined position; adjusting the set scanning trajectory when the position of the target area in the ultrasound image does not belong to the predetermined position; and controlling the mechanical arm to drive the probe to move based on the adjusted scanning trajectory.

Preferably, before controlling the mechanical arm to drive the probe to move based on the set scanning trajectory, the method further includes: determining a part to be examined, and converting initial position coordinates of the part to be examined in a first coordinate system where a hospital bed is located into initial position coordinates of the part to be examined in a second coordinate system where the ultrasound scanning device is located; and generating the set scanning trajectory based on the initial position coordinates of the part to be examined in the second coordinate system, wherein the set scanning trajectory includes a plurality of position coordinates.

Preferably, the converting initial position coordinates of the part to be examined in the first coordinate system where the hospital bed is located into initial position coordinates of the part to be examined in the second coordinate system where the ultrasound scanning device is located includes: calculating a conversion matrix $R_{trans}$ between the first coordinate system and the second coordinate system; calculating the initial position coordinates of the part to be examined in the second coordinate system where the ultrasound scanning device is located by using a formula $p_1 = R_{trans} p_0 + p_{trans}$ according to the conversion matrix $R_{trans}$; Wherein $p_1$ represents an initial position vector of the part to be examined in the second coordinate system, $R_{trans}$ represents the conversion matrix between the first coordinate system and the second coordinate system, $p_0$ represents an initial position vector of the part to be examined in the first coordinate system, and $p_{trans}$ represents a position vector of an origin of the first coordinate system relative to the second coordinate system.

Preferably, the execution mechanism further includes a force sensor, the method further includes: controlling a pressure value between the probe and the part to be examined to be a constant value, including: sensing an actual pressure value between the probe and the part to be examined in each control cycle using the force sensor; calculating a position change amount $\Delta p$ of position change using a preset position change formula according to the actual pressure value, wherein $\Delta p = K_p * e_f + K_d * \Delta e_f$; Wherein $K_p$ represents a preset proportional value and $K_d$ represents a preset differential gain; $e_f$ represents a pressure error value between a preset target pressure value and the actual pressure value in a control cycle; $\Delta e_f$ represents an amount of error change between a pressure error value corresponding to a current control cycle and a pressure error value corresponding to a previous control cycle; and controlling the mechanical arm to drive the probe to make a position change with the position change amount $\Delta p$ in a vertical direction based on the second coordinate system.

Preferably, the controlling the mechanical arm to drive the probe to make the position change with the position change amount $\Delta p$ in the vertical direction based on the second coordinate system includes: controlling the mechanical arm to drive the probe to move downward in the vertical direction based on the second coordinate system, when the position change amount $\Delta p$ is a positive value; controlling the mechanical arm to drive the probe to move upward in the vertical direction based on the second coordinate system, when the position change amount $\Delta p$ is a negative value; and not controlling the mechanical arm to drive the probe to move in the vertical direction based on the second coordinate system, when the position change amount $\Delta p$ is 0.

Preferably, the execution mechanism further includes a force sensor, the method further includes: sensing a lateral impact force F received by the probe using the force sensor; calculating a position change amount S according to the lateral impact force F received by the probe, wherein the position change amount $S = F * K$. F represents a magnitude of the lateral impact force, and K is a known coefficient; and controlling the mechanical arm to drive the probe to move a preset distance along a direction of the lateral impact force, according to a magnitude relationship between the calculated position change amount S and a preset maximum position change amount.

Preferably, when the calculated position change amount S is less than or equal to the maximum position change amount, the preset distance is equal to the calculated position change amount; when the calculated position change amount is greater than the maximum position change amount, the preset distance is equal to the maximum position change amount.

Preferably, the controlling the mechanical arm to drive the probe to move the preset distance along the direction of the lateral impact force includes: calculating a moving speed according to a preset control cycle and the preset distance;

and controlling the mechanical arm to drive the probe to move the preset distance along the direction of the lateral impact force at the moving speed.

Preferably, the calculating the position of the target area in the ultrasound image, and determining whether the position of the target area in the ultrasound image belongs to the predetermined position includes: determining a center of a smallest circumscribed circle of the target area; calculating position coordinates of the determined center in the ultrasound image; determining that the position of the target area in the ultrasound image belongs to the predetermined position, when an abscissa and an ordinate corresponding to the determined center are the same as those corresponding to the center position of the ultrasound image, or when a difference value between the abscissa corresponding to the determined center and the abscissa corresponding to the center position of the ultrasound image is less than a preset value and a difference value between the ordinate corresponding to the determined center and the ordinate corresponding to the center position of the ultrasound image is less than the preset value; and determining that the position of the target area in the ultrasound image does not belong to the predetermined position, when the difference value between the abscissa corresponding to the determined center and the abscissa corresponding to the center position of the ultrasound image is greater than or equal to the preset value and/or the difference value between the ordinate corresponding to the determined center and the ordinate corresponding to the center position of the ultrasound image is greater than or equal to the preset value.

Preferably, the adjusting the set scanning trajectory includes: calculating a first difference value between the abscissa corresponding to the position of the target area in the ultrasound image and the abscissa corresponding to the predetermined position; calculating a second difference value between the ordinate corresponding to the position of the target area in the ultrasound image and the ordinate corresponding to the predetermined position; and adjusting the scanning trajectory based on the first difference value and the second difference value.

A second aspect of the present disclosure provides an ultrasound scanning device, including: a processor; and a storage device storing one or more computer programs, which when executed by the processor, cause the processor to perform an ultrasound scanning control method.

A third aspect of the present disclosure provides a non-volatile storage medium having computer programs stored thereon, when the computer programs are executed by a processor, the processor is configured to perform an ultrasound scanning control method.

A fourth aspect of the present disclosure provides an ultrasound scanning control system run in an ultrasound scanning device which including an execution mechanism, the execution mechanism including a mechanical arm and a probe, the ultrasound scanning control system including: a control module, which is used to control the mechanical arm to drive the probe to move based on a set scanning trajectory; the control module is further used to controlling the probe to collect an ultrasound image; the control module is further used to identify a target area from the ultrasound image; the control module is further used to calculate a position of the target area in the ultrasound image, and determining whether the position of the target area in the ultrasound image belongs to a predetermined position; the control module is further used to adjust the set scanning trajectory when the position of the target area in the ultrasound image does not belong to the predetermined position; and the control module is further used to control the mechanical arm to drive the probe to move based on the adjusted scanning trajectory.

The ultrasound scanning control method, the ultrasound scanning control system, the ultrasound scanning device, and the storage medium provided by the present disclosure provides can realize automatic scanning of the ultrasound scanning device and can realize flexible interaction between the ultrasound scanning device and a patient.

BRIEF DESCRIPTION OF THE DRAWINGS

In order to more clearly describe the technical solutions in the embodiments of the present disclosure or the prior art, the following briefly introduces the drawings that need to be used in the description of the embodiments or the prior art. Obviously, the drawings in the following description are only embodiments of the present disclosure. For those of ordinary skill in the art, other drawings can be obtained according to the provided drawings without creative work.

The following embodiments further illustrates the present disclosure in conjunction with the above-mentioned drawings.

DETAILED DESCRIPTION

In order to be able to understand the object, features and advantages of the embodiments of the present disclosure, implementations of the disclosure will now be described, by way of embodiments only, with reference to the drawings. It should be noted that non-conflicting details and features in the embodiments of the present disclosure may be combined with each other.

In the following description, specific details are explained in order to make the embodiments of the present disclosure understandable. The described embodiments are only a portion of, rather than all of the embodiments of the present disclosure of them. Based on the embodiments of the present disclosure, other embodiments obtained by a person of ordinary skill in the art without creative work shall be within the scope of the present disclosure.

Unless otherwise defined, all technical terms used herein have the same meaning as commonly understood by one of ordinary skill in the art. The technical terms used herein are not to be considered as limiting the scope of the embodiments.

Figure 1:
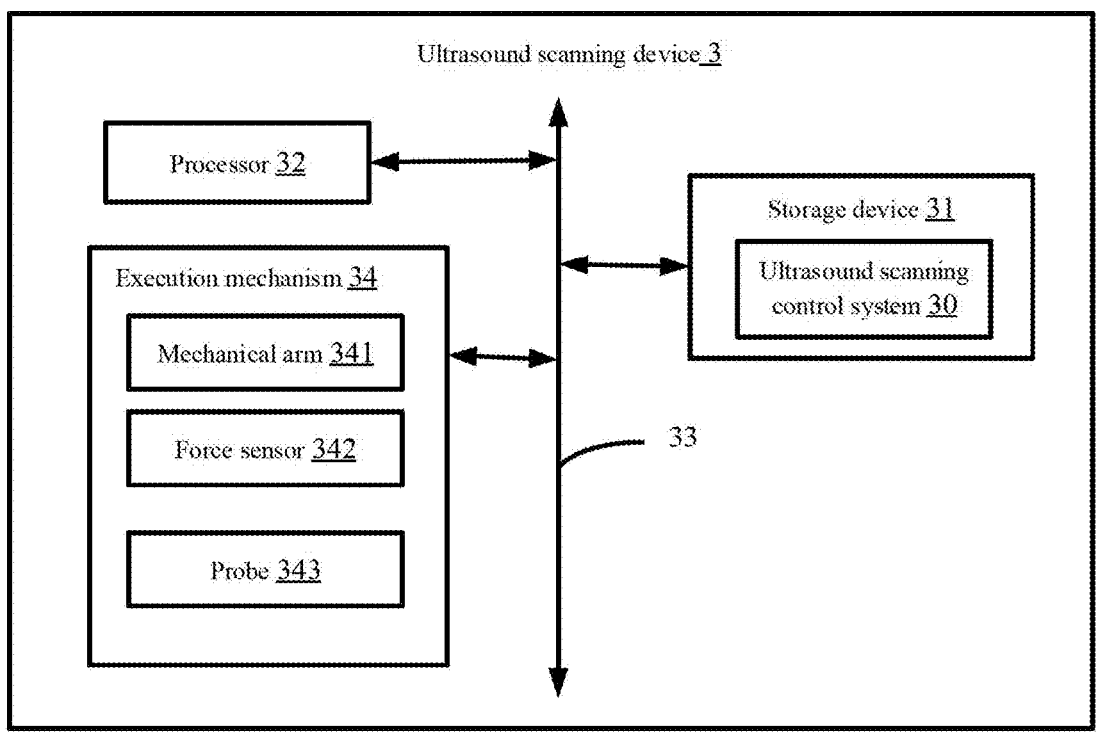
FIG. 1 is a structural diagram of an ultrasound scanning device provided by a preferred embodiment of the present disclosure.

Refer to FIG. 1, which is a structural diagram of an ultrasound scanning device provided by a preferred embodiment of the present disclosure. Please also refer to FIG. 2A, which is an application environment diagram of the ultrasound scanning control method provided by the preferred embodiment of the present disclosure.

In one embodiment, the ultrasound scanning device 3 can perform a medical ultrasound examination on a tested object lying on a hospital bed 4.

In a preferred embodiment of the present disclosure, the ultrasound scanning device 3 includes a storage device 31, at least one processor 32, at least one communication bus 33, and an execution mechanism 34 that are electrically connected to each other.

Those skilled in the art should understand that the structure of the ultrasound scanning device 3 shown in FIG. 1 does not constitute a limitation of the embodiment of the present disclosure. It may be a bus-type structure or a star-shaped structure. The ultrasound scanning device 3 may also include more or less other hardware or software than shown, or have different component arrangements. For example, the ultrasound scanning device 3 may also include a display screen.

In some embodiments, the ultrasound scanning device 3 includes a terminal that can automatically perform numerical calculation and/or information processing according to pre-set or stored instructions, and its hardware includes, but is not limited to, a microprocessor and an application specific integrated circuit, programmable gate arrays, digital processors and embedded devices, etc.

It should be noted that the ultrasound scanning device 3 is only an example. If other existing or future electronic products can be adapted to the present disclosure, they should also be included in the scope of protection of the present disclosure and be included by reference.

In some embodiments, the storage device 31 may be used to store program codes and various data of computer programs. For example, the storage device 31 may be used to store an ultrasound scanning control system 30 installed in the ultrasound scanning device 3 and implement completion of storing programs or data during an operation of the ultrasound scanning device 3. The storage device 31 may include Read-Only Memory (ROM), Programmable Read-Only Memory (PROM), and Erasable Programmable Read-Only Memory. EPROM), One-time Programmable Read-Only Memory (OTPROM), Electronically-Erasable Programmable Read-Only Memory (EEPROM), Compact Disc (Compact Disc) Read-Only Memory (CD-ROM) or other optical disk storage, disk storage, magnetic tape storage, or any other non-transitory computer-readable storage medium that can be used to carry or store data.

In some embodiments, the at least one processor 32 may be composed of an integrated circuit. For example, the at least one processor 32 can be composed of a single packaged integrated circuit or can be composed of multiple packaged integrated circuits with the same function or different function. The at least one processor 32 includes one or more central processing units (CPUs), one or more microprocessors, one or more digital processing chips, one or more graphics processors, and various control chips. The at least one processor 32 is a control unit of the ultrasound scanning device 3. The at least one processor 32 uses various interfaces and lines to connect various components of the ultrasound scanning device 3, and executes programs or modules or instructions stored in the storage device 31, and invokes data stored in the storage device 31 to perform various functions of the ultrasound scanning device 3 and to process data, for example, to perform a function of ultrasound scanning detection on the patient lying on the bed 4. (Specific details will be introduced later).

Figure 2A:
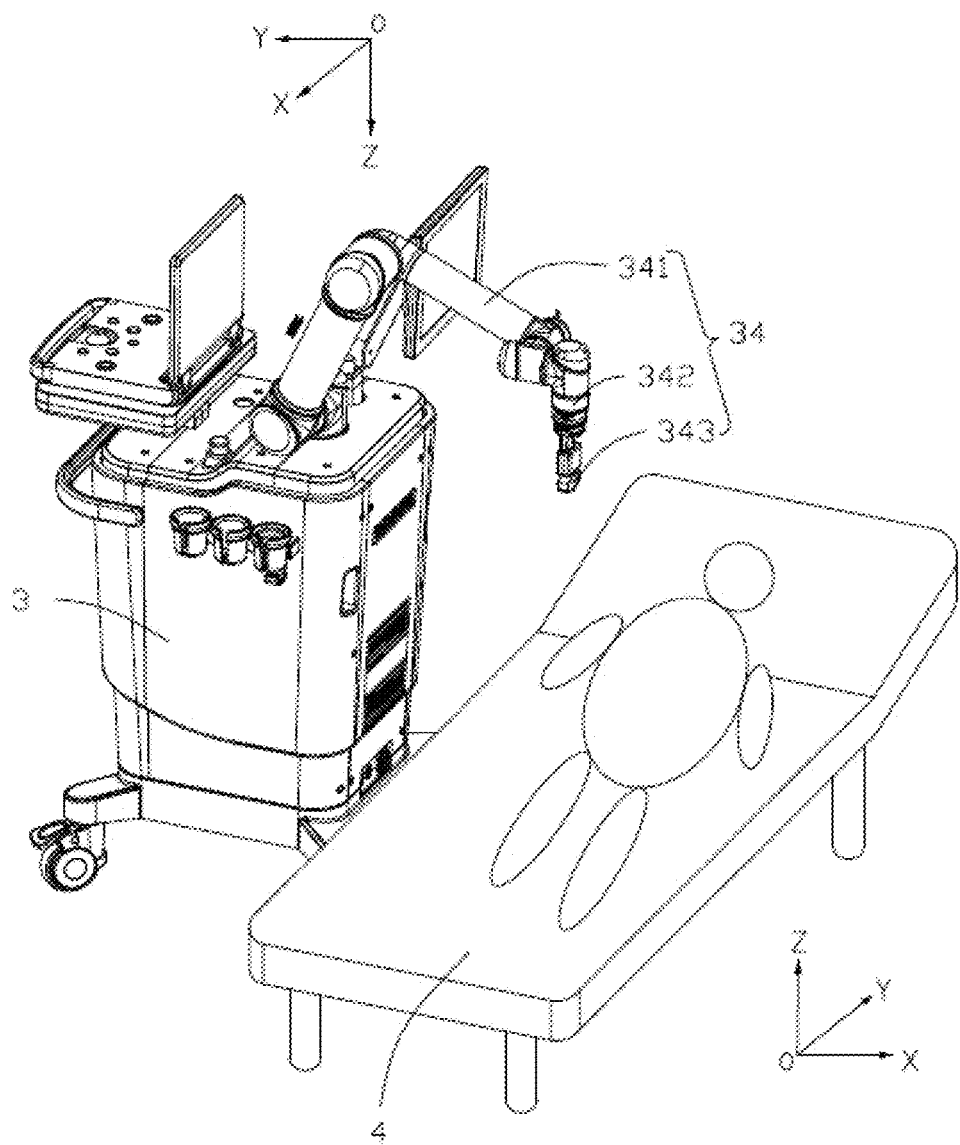
FIG. 2A is a diagram of an application environment of an ultrasound scanning control method provided by the preferred embodiment of the present disclosure.

It should be noted that, in order to facilitate the patient to understand a specified lying posture of an ultrasound examination, before the ultrasound examination, corresponding instructions may be given on the hospital bed 4 in advance. As shown in FIG. 2A, the patient can be instructed on the hospital bed 4 in a diagram or in other form on how to lie down, so that the patient can lie down on the hospital bed 4 for ultrasound examination according to the instructions.

In some embodiments, the at least one communication bus 33 is configured to implement a communication connection between the storage device 31 and the at least one processor 32, and the like.

As shown in FIG. 2A, in this embodiment, the execution mechanism 34 of the ultrasound scanning device 3 includes a mechanical arm 341, a force sensor 342, and a probe 343. Preferably, the mechanical arm 341 is a six-degree-of-freedom robotic arm. The force sensor 342 is arranged at an end of the mechanical arm 341, and the probe 343 is arranged under the force sensor 342. The force sensor 342 may be directly or indirectly connected to the probe 343. The force sensor 342 is used to sense a pressure value between the probe 343 and a part to be examined when the probe 343 is in contact with the part to be examined.

In an embodiment, the force sensor 342 can also sense a lateral impact force received by the probe 343.

In one embodiment, the ultrasound scanning control system 30 can convert initial position coordinates of the part to be examined in a first coordinate system where the hospital bed 4 is located into initial position coordinates of the part to be examined in a second coordinate system where the ultrasound scanning device 3 is located. The ultrasound scanning control system 30 can generate a scanning trajectory for the probe 343 based on the initial position coordinates of the part to be examined in the second coordinate system, and can control the mechanical arm 341 to drive the probe 343 to move based on the scanning trajectory. Details will be introduced later.

Figure 2B:
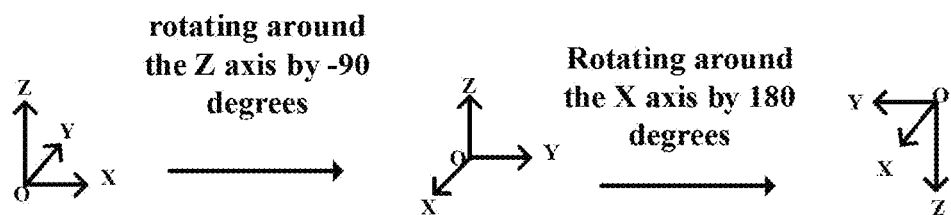
FIG. 2B illustrates a conversion of a first coordinate system to a second coordinate system.

In order to clearly illustrate the present disclosure, as shown in FIG. 2A and FIG. 2B, in this embodiment, an OZ axis of the first coordinate system is a plumb upward direction, an OX axis of the first coordinate system is a horizontal direction directed to the right, and a Y axis of the first coordinate system is a direction that is vertical to a plane formed by the OX axis and the OZ axis. In this embodiment, the second coordinate system is a coordinate system obtained by first rotating the first coordinate system around the Z axis by −90 degrees, and then rotating around the X axis by 180 degrees. It should be noted that the establishment of the first coordinate system and the second coordinate system is only an example, and should not be construed as a limitation to the invention.

In this embodiment, the ultrasound scanning control system 30 may include one or more modules, and the one or more modules are stored in the storage device 31 and are executed by one or more processors (for example, the processor 32) to complete the present disclosure.

Figure 3:
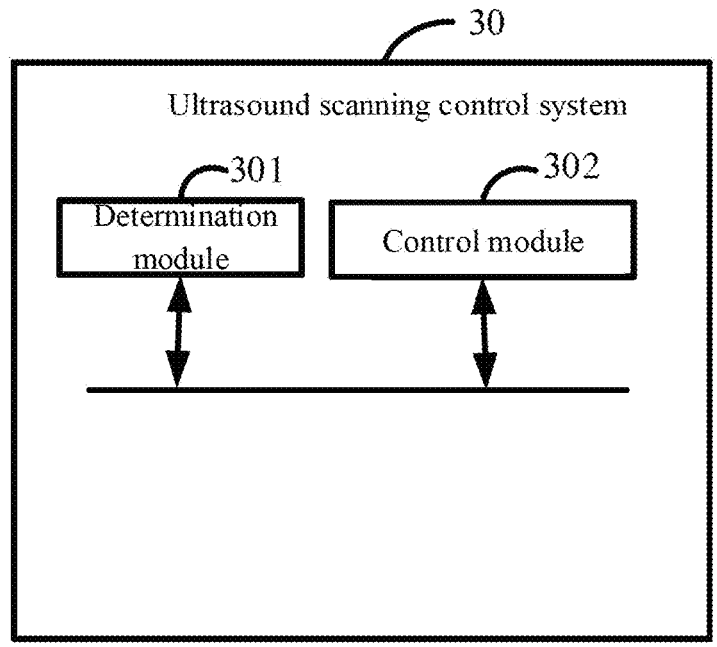
FIG. 3 is a schematic diagram of an ultrasound scanning control system provided by a preferred embodiment of the present disclosure.

For example, referring to FIG. 3, the ultrasound scanning control system 30 includes a determination module 301 and a control module 302. The module referred to in the present disclosure is a program segment of a computer program that can complete a specified function. Detailed function of each module will be described in detail in conjunction with the flowchart in FIG. 4.

Figure 4:
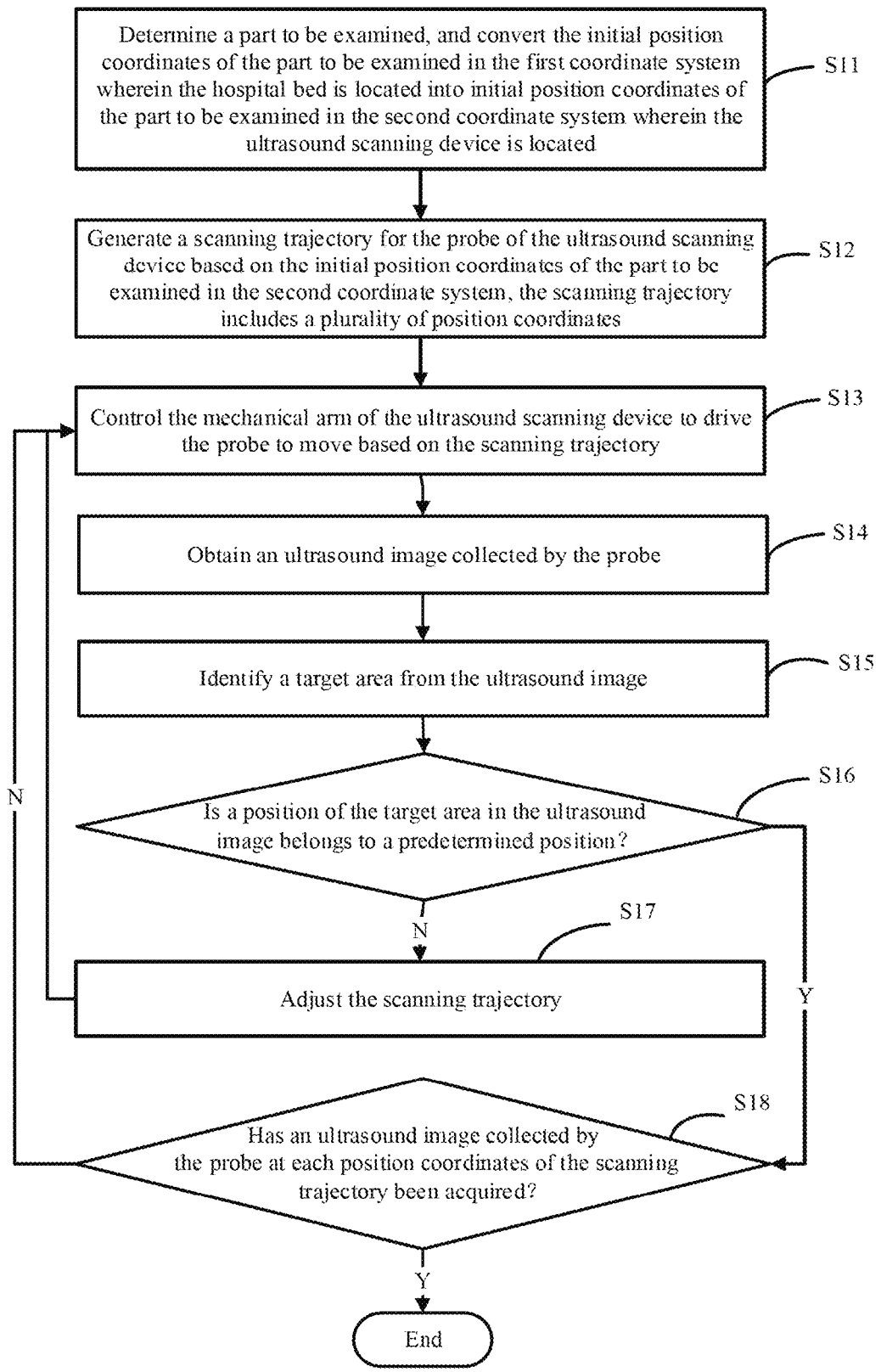
FIG. 4 is a flowchart of an ultrasound scanning control method provided by a preferred embodiment of the present disclosure.

FIG. 4 is a flowchart of an ultrasound scanning control method provided by a preferred embodiment of the present disclosure.

In this embodiment, the ultrasound scanning control method can be applied to the ultrasound scanning device 3. For the ultrasound scanning device 3 that needs to execute a function of the ultrasound scanning control, the ultrasound scanning device 3 can directly integrate the function of the ultrasound scanning control provided by the method of the present disclosure, or the function of the ultrasound scanning control can be in a form of a Software Development Kit (SDK) run on the ultrasound scanning device 3.

As shown in FIG. 4, the ultrasound scanning control method includes the following blocks. According to different requirements, the order of the blocks in the flowchart can be changed, and some blocks can be omitted.

Block S11, the determining module 301 determines a part to be examined, and converts the initial position coordinates of the part to be examined in the first coordinate system where the hospital bed 4 is located into initial position coordinates of the part to be examined in the second coordinate system where the ultrasound scanning device 3 is located.

In this embodiment, the determining module 301 can determine the part to be examined in response to input of a user (for example, an ultrasound doctor).

For example, the determining module 301 may arrange and display various parts (such as the heart, thyroid, etc.) that can be scanned by ultrasound on a display screen of the ultrasound scanning device 3, and then determine the part to be examined according to user selection. Thus, the part to be examined can be determined.

In an embodiment, the converting the initial position coordinates of the part to be examined in the first coordinate system where the hospital bed 4 is located into initial position coordinates of the part to be examined in the second coordinate system where the ultrasound scanning device 3 is located include (a1)-(a2):
 (a1) Calculating a conversion matrix $R_{trans}$ between the first coordinate system and the second coordinate system.
 (a2) Calculating the initial position coordinates of the part to be examined in the second coordinate system where the ultrasound scanning device 3 is located by using a formula $p_1 = R_{teans}p_0 + p_{trans}$ according to the conversion matrix $R_{trans}$.

Wherein $p_1$ represents an initial position vector of the part to be examined in the second coordinate system, $R_{trans}$ represents the conversion matrix between the first coordinate system and the second coordinate system, $p_0$ represents an initial position vector of the part to be examined in the first coordinate system, and $p_{trans}$ represents a position vector of an origin of the first coordinate system relative to the second coordinate system.

In this embodiment, the initial position vectors $p_0$ of different parts to be examined in the first coordinate system are different, and the initial position vector $p_0$ of each part to be examined in the first coordinate system can be preset. Therefore, once the part to be examined is determined, the initial position vector $p_0$ corresponding to the part to be examined can be determined.

In one embodiment, referring to FIG. 2A and FIG. 2B, the second coordinate system is a coordinate system that is obtained by first rotating the first coordinate system around the Z axis by −90 degrees, and then rotating the X axis by 180 degrees.

In one embodiment, the conversion matrix $$R_{trans} = R_Z\left(-\frac{\pi}{2}\right)R_X\pi.$$

Wherein $$R_Z(-\pi/2) = \begin{bmatrix} \cos(-\pi/2) & -\sin(-\pi/2) & 0 \\ \sin(-\pi/2) & \cos(-\pi/2) & 0 \\ 0 & 0 & 1 \end{bmatrix},$$

$$R_X\pi = \begin{bmatrix} 1 & 0 & 0 \\ 0 & \cos\pi & -\sin\pi \\ 0 & \sin\pi & \cos\pi \end{bmatrix}.$$

Block S12, the determination module 301 generates a scanning trajectory for the probe 343 of the ultrasound scanning device 3 based on the initial position coordinates of the part to be examined in the second coordinate system. In this embodiment, the determining module 301 uses a plurality of position coordinates to define the scanning trajectory. In other words, the scanning trajectory includes a plurality of position coordinates.

In this embodiment, the determination module 301 sets the initial position coordinates of the part to be examined in the second coordinate system as a starting point of the scanning trajectory. In other words, the plurality of position coordinates include the initial position coordinates of the part to be examined in the second coordinate system, and the initial position coordinates of the part to be examined in the second coordinate system is set as a starting point of the probe 343.

For example, suppose that the scanning trajectory is traj=$\{p_1, p_2, p_3 \ldots p_n\}$, then $p_1, p_2, p_3 \ldots p_n$ are the position coordinates that define the scanning trajectory, $p_1$ is the initial position coordinates of the part to be examined in the second coordinate system, i.e., the starting point of the probe 343.

Block S13, the control module 302 controls the mechanical arm 341 of the ultrasound scanning device 3 to drive the probe 343 to move based on the scanning trajectory.

For example, the control module 302 controls the mechanical arm 341 of the ultrasound scanning device 3 to drive the probe 343 to first move to the starting point of the scanning trajectory, i.e., move to the position coordinates $p_1$.

In one embodiment, when the control module 302 controls the mechanical arm 341 of the ultrasound scanning device 3 to drive the probe 343 to move based on the scanning trajectory, the control module 302 also controls a pressure value between the probe 343 and the part to be examined to be a constant value.

In one embodiment, the controlling the pressure value between the probe 343 and the part to be examined to a constant value includes (b1)-(b3):
 (b1) Sensing an actual pressure value between the probe 343 and the part to be examined in each control cycle (for example, 8 ms) using the force sensor 342;
 (b2) Calculating a position change amount Δp of position change using a preset position change formula according to the actual pressure value, wherein $\Delta p = K_P * e_f + K_d * \Delta e_f$.

Wherein $K_p$ represents a preset proportional value and $K_d$ represents a preset differential gain. That is, $K_p$ and $K_d$ are both known numbers. $e_f$ represents a pressure error value between a preset target pressure value and the actual pressure value (i.e., a difference value between the target pressure value and the actual pressure value) in a control cycle. $\Delta e_f$ represents an amount of error change between a pressure error value corresponding to a current control cycle and a pressure error value corresponding to a previous control cycle (i.e., a difference value between the pressure error values corresponding to two adjacent control cycles).

(b3) Controlling the mechanical arm 341 to drive the probe 343 to make a position change with the position change amount Δp in a vertical direction based on the second coordinate system, for example, move along the Z axis of the second coordinate system with the position change amount Δp.

It should be noted that the vertical direction in the embodiment refers to a plumb direction.

Specifically, the controlling the mechanical arm 341 to drive the probe 343 to make a position change with the position change amount Δp in a vertical direction based on the second coordinate system includes (b31)-(b33):

(b31) When the position change amount Δp is a positive value, controlling the mechanical arm 341 to drive the probe 343 to move downward in the vertical direction based on the second coordinate system.

(b32) When the position change amount Δp is a negative value, controlling the mechanical arm 341 to drive the probe 343 to move upward in the vertical direction based on the second coordinate system.

(b33) When the position change amount Δp is 0, not control the mechanical arm 341 to drive the probe 343 to move in the vertical direction based on the second coordinate system.

In one embodiment, when the control module 302 controls the mechanical arm 341 of the ultrasound scanning device 3 to drive the probe 343 to move based on the scanning trajectory, the control module 302 also senses a lateral impact force F received by the probe 343 using the force sensor 342.

In one embodiment, when the force sensor 342 obtains the lateral impact force F received by the probe 343, the control module 302 also triggers a force protection strategy according to the lateral impact force F received by the probe 343, to achieve a flexible interaction between the probe 343 and the patient.

In one embodiment, the triggering the force protection strategy according to the lateral impact force F received by the probe 343 includes (c1)-(c3):

(c1) Calculating a position change amount S according to the lateral impact force F received by the probe 343, wherein the position change amount S=F*K. F represents a magnitude of the lateral impact force. K is a known coefficient.

In this embodiment, a magnitude of K is related to the part to be examined of the tested object. For example, a magnitude of K that corresponds to a human abdomen equals 0.0001, and a magnitude of K that corresponds to a human thyroid equals 0.0005.

(c2) Determining a magnitude relationship between the calculated position change amount and a preset maximum position change amount (for example, 0.003 m).

(c3) Controlling the mechanical arm 341 to drive the probe 343 to move a preset distance along a direction of the lateral impact force, according to the magnitude relationship between the calculated position change amount and the maximum position change amount.

Wherein, when the calculated position change amount is less than or equal to the maximum position change amount, the preset distance is equal to the calculated position change amount. When the calculated position change amount is greater than the maximum position change amount, the preset distance is equal to the maximum position change amount.

It should be noted that setting the maximum position change is to prevent the probe 343 from being separated from the part to be examined (i.e., the patient's skin) due to excessive lateral impact force of the probe 343, thereby causing ultrasound images are not continuous and other problems appear.

In one embodiment, the controlling the mechanical arm 341 to drive the probe 343 to move a preset distance along a direction of the lateral impact force, according to the magnitude relationship between the calculated position change amount and the maximum position change amount include:

(c31) Calculating a moving speed according to a preset control cycle and the preset distance.

For example, assuming that the control cycle is 8 ms and the preset distance is 0.003 m, then the moving speed is 0.375 m/s.

(c32) Controlling the mechanical arm 341 to drive the probe 343 to move the preset distance along the direction of the lateral impact force at the moving speed.

Block S14, When the probe 343 currently moves to any one position coordinates of the scanning trajectory, the control module 302 controls the probe 343 to collect an ultrasound image, thereby an ultrasound image corresponding to the current position coordinates is obtained.

For example, assuming that the probe 341 currently moves to the starting point of the scanning trajectory, the control module 302 controls the probe 343 to collect at least one ultrasound image corresponding to the starting position.

Block S15, the control module 302 identifies a target area from the ultrasound image.

In one embodiment, the control module 302 may identify the target area from the ultrasound image using an instance segmentation algorithm.

In one embodiment, the identifying the target area from the ultrasound image using an instance segmentation algorithm includes (d1)-(d6):

(d1) extracting features by inputting the ultrasound image into a regional convolutional neural network (R-CNN);

(d2) Generating proposal windows (proposals) in a regional proposal network (RPN), wherein N proposal windows are generated for each ultrasound image;

(d3) Mapping the proposal windows to convolution feature map of a last layer of the R-CNN;

(d4) Generating a fixed-size feature map corresponding to each region of interest (RoI) through the Pyramid RoI Align (ROI Align);

(d5) Performing a full connection on the fixed-size feature maps to complete target classification and bounding box regression;

(d6) Setting classification error, detection error and segmentation error as the total loss function, and use stochastic gradient descent to optimize the loss function.

It should be noted that, in this embodiment, a back propagation formula of ROI Align is:

$$\frac{\partial L}{\partial x_i} = \sum_r \sum_j [d(i, i*(r, j)) < 1](1 - \Delta h)(1 - \Delta \omega)\frac{\partial L}{\partial y_{rj}}.$$

In this embodiment, $x_i*(r, j)$ is the coordinate position of a float. Prior to pooling FIG feature, each of the $x_i*(r, j)$ are smaller than the horizontal and vertical coordinates of a point corresponding thereto should receive the return point $y_{r,j}$ gradient. d(i, i*(r, j)) represents a distance between two points. Δh and Δω represents $x_i$ and $x_i$*(r, j) of the difference between horizontal and vertical coordinates, herein incorporated by bilinear interpolation coefficient in the original gradient on.

In other embodiments, the control module 302 may also use a template matching method to identify the target area from the ultrasound image. That is, the control module 302 can match the ultrasound image with a pre-stored template image, and identify the target area according to an image similarity. This is the prior art in the field and will not be repeated here.

Block S16, the control module 302 calculates a position of the target area in the ultrasound image, and determines whether the position of the target area in the ultrasound image is a predetermined position. When the position of the target area in the ultrasound image does not belong to the predetermined position, block S17 is executed. When the position of the target area in the ultrasound image belongs to the predetermined position, block S18 is executed.

In one embodiment, the predetermined position refers to a center position of the ultrasound image.

In an embodiment, the calculating the position of the target area in the ultrasound image and determining whether the position of the target area in the ultrasound image is a predetermined position includes (e1)-(e4):
(e1) Determining a center of a smallest circumscribed circle of the target area.
(e2) Calculating position coordinates of the determined center in the ultrasound image.

In an implementation, a two-dimensional coordinate system may be established based on the ultrasound image, for example, the two-dimensional coordinate system is established by setting a corner of the ultrasound image as the origin, setting a horizontal direction of the ultrasound image as the X axis, and setting the vertical direction as the Y axis. Thus, the position coordinates of the determined center in the ultrasound image can be determined.
(e3) When an abscissa and an ordinate corresponding to the determined center are the same as those corresponding to the center position of the ultrasound image, or when a difference value between the abscissa corresponding to the determined center and the abscissa corresponding to the center position of the ultrasound image is less than a preset value and a difference value between the ordinate corresponding to the determined center and the ordinate corresponding to the center position of the ultrasound image is less than the preset value, it is determined that the position of the target area in the ultrasound image belongs to the predetermined position.
(e4) When the difference value between the abscissa corresponding to the determined center and the abscissa corresponding to the center position of the ultrasound image is greater than or equal to the preset value and/or the difference value between the ordinate corresponding to the determined center and the ordinate corresponding to the center position of the ultrasound image is greater than or equal to the preset value, it is determined that the position of the target area in the ultrasound image does not belong to the predetermined position.

Block S17, when the position of the target area in the ultrasound image does not belong to the predetermined position, the control module 302 adjusts the scanning trajectory.

In an embodiment, the adjusting the scanning trajectory includes (f1)-(f3):
(f1) Calculating a first difference value between the abscissa corresponding to the position of the target area in the ultrasound image and the abscissa corresponding to the predetermined position;
(f2) Calculating a second difference value between the ordinate corresponding to the position of the target area in the ultrasound image and the ordinate corresponding to the predetermined position;
(f3) Adjusting the scanning trajectory based on the first difference value and the second difference value.

For example, assuming that the first difference value is 1 and the second difference value is 0, then adding the first difference value to the abscissa corresponding to each position coordinates of the scanned trajectory, and adding the second difference value to the ordinate corresponding to each position coordinates of the scanned trajectory, so as to realize the adjustment of the scanning trajectory. After block S17 is executed, the process returns to block S13. It should be noted that when the process returns to block S13 from block S17, the control module 302 controls the mechanical arm 341 to drive the probe 343 to move based on the adjusted scanning trajectory.

For example, assuming that the probe 343 is currently located at the position $p_1$ of the scanning trajectory before adjustment, in the adjusted scanning trajectory, the position $p_1$ is correspondingly adjusted to be $p_1'$, then the control module 302 controls the mechanical arm 341 to drive the probe 343 to move to the adjusted position $p_1'$ of the adjusted scanning trajectory.

Block S18, the control module 302 determines whether an ultrasound image collected by the probe 343 at each position coordinates of the scanning trajectory has been acquired. When the image collected by the probe 343 at each position coordinates of the scanning trajectory has been acquired, the process ends. When not all the ultrasound image collected by the probe 343 at each position coordinates of the scanning trajectory has been acquired (i.e., the probe 343 has not completed the scanning trajectory), block S13 is executed.

It should be noted that when the process goes to block S13 from the block S18, at the block S13, the control module 302 controls the mechanical arm 341 to drive the probe 343 to move from a current position coordinates to a next position coordinates of the scanning trajectory. For example, controlling the mechanical arm 341 to drive the probe 343 to move from a position of $p_1$ to a position of $p_2$.

Figure 5:
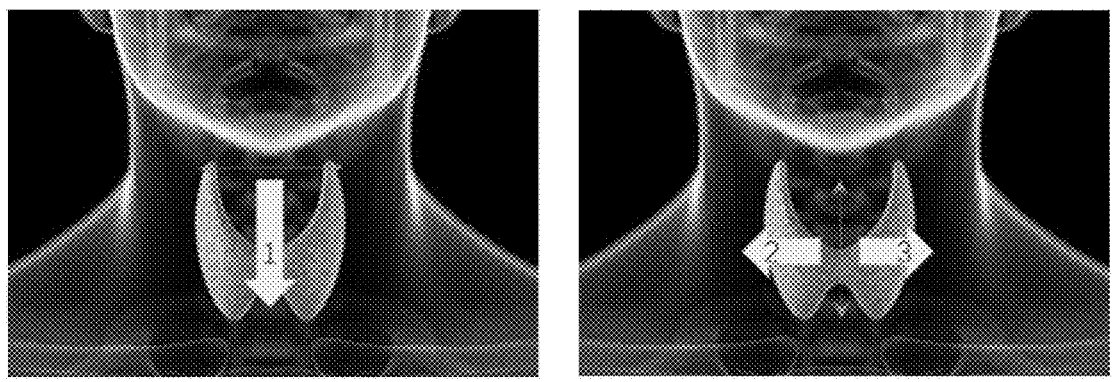
FIG. 5 illustrates a scanning process of a thyroid gland.

In order to facilitate those skilled in the art to understand the present disclosure, for example, referring to FIG. 5, taking the scanning of the thyroid as an example. In the scanning process, first scanning a middle part of the thyroid according to step 1 shown in FIG. 5, and then scanning a left side and a right side of the thyroid according to step 2 and step 3 respectively shown in FIG. 5. According to this scanning process, the ultrasound scanning control system 30 generates a corresponding scanning trajectory, identifies an area of the thyroid using image processing algorithms when the probe executes scanning according to the scanning trajectory, and adjusts the scanning trajectory in real time according to the identified area, such that fully automatic scanning of the thyroid gland is achieved.

According to the above description, the ultrasound scanning control method of the embodiment of the present disclosure includes controlling the mechanical arm to drive the probe to move based on a set scanning trajectory; controlling the probe to collect ultrasound images; and identifying a target area from the ultrasound image; calculating a position of the target area in the ultrasound image, and determining whether the position of the target area in the ultrasound image belongs to a predetermined position; adjusting the scanning trajectory when the position of the target area in the ultrasound image does not belong to the predetermined position; and controlling the mechanical arm to drive the probe to move based on the adjusted scanning trajectory, so as to realize an automatic scanning of the ultrasound scanning device, and realize a flexible interaction between the patient and the ultrasound scanning device.

In some embodiments according to the present disclosure, it should be understood that the disclosed non-volatile readable storage medium, device and method can be implemented in other ways. For example, the device embodiments described above are merely schematic, for example, the division of the modules is only one logical function division, and actual implementation may have other division manners.

The modules described as separate components may or may not be physically separated, and the components displayed as the modules may or may not be physical modules, that is, they may be located in one place, or may be distributed in multiple network modules. Some or all of the modules may be selected according to actual requirements to realize the purpose of the solution of the embodiments.

In addition, each of the functional modules according to the respective embodiments of the present disclosure may be integrated in one processing module, or each module may physically exist alone, or two or more modules may be integrated in one module. The above-mentioned integrated module can be implemented either in a form of hardware or in a form of hardware plus software functional modules.

To those skilled in the art, obviously, the present disclosure is not limited to the details of the foregoing exemplary embodiments, and the present disclosure can be implemented in other specific forms without departing from the spirit or basic features of the present disclosure. Therefore, from any point of view, the embodiments should be regarded as exemplary and non-restrictive, and the scope of the present disclosure is defined by the appended claims rather than the above description, and thus, all changes that fall within the meanings and scopes of equivalent elements of the claims are intended to be encompassed within the present disclosure. No reference signs in the claims should be construed as limiting the claims involved. In addition, obviously the word "include" does not exclude other units or steps, and the singular does not exclude the plural. Multiple units or devices stated in the device claims may also be implemented by one unit or one device through software or hardware. Words such as first and second are used to denote names, but do not denote any specific order.

Finally, it should be noted that the above embodiments are only used for illustrating the technical solutions of the present disclosure rather than for limitations. Although the present disclosure is described in detail with reference to the preferred embodiments, those of ordinary skill in the art should understand that they still can make modifications or equivalent substitutions to the technical solutions of the present disclosure without departing from the spirit and scope of the technical solutions of the present disclosure.

What is claimed is:

1. An ultrasound scanning control method applied to an ultrasound scanning device which comprising an execution mechanism, the execution mechanism comprising a force sensor, a mechanical arm and a probe, the ultrasound scanning control method comprising:

controlling the mechanical arm to drive the probe to move based on a set scanning trajectory;

controlling the probe to collect an ultrasound image;

identifying a target area from the ultrasound image;

calculating a position of the target area in the ultrasound image, and determining whether the position of the target area in the ultrasound image belongs to a predetermined position;

controlling the mechanical arm to drive the probe to move based on the set scanning trajectory in response that the position of the target area in the ultrasound image belong to the predetermined position;

adjusting the set scanning trajectory in response that the position of the target area in the ultrasound image does not belong to the predetermined position; and controlling the mechanical arm to drive the probe to move based on the adjusted scanning trajectory;

wherein the ultrasound scanning control method further comprises:

sensing a lateral impact force F received by the probe using the force sensor;

calculating a position change amount S according to the lateral impact force F received by the probe, wherein the calculated position change amount $S=F*K$, F represents a magnitude of the lateral impact force, and K is a known coefficient; and controlling the mechanical arm to drive the probe to move a preset distance along a direction of the lateral impact force, according to a magnitude relationship between the calculated position change amount S and a preset maximum position change amount.

2. The ultrasound scanning control method of claim 1, wherein before controlling the mechanical arm to drive the probe to move based on the set scanning trajectory, further comprising:

determining a part to be examined, and converting initial position coordinates of the part to be examined in a first coordinate system wherein a hospital bed is located into initial position coordinates of the part to be examined in a second coordinate system wherein the ultrasound scanning device is located; and generating the set scanning trajectory based on the initial position coordinates of the part to be examined in the second coordinate system, wherein the set scanning trajectory comprises a plurality of position coordinates.

3. The ultrasound scanning control method of claim 2, wherein the converting initial position coordinates of the part to be examined in the first coordinate system wherein the hospital bed is located into initial position coordinates of the part to be examined in the second coordinate system wherein the ultrasound scanning device is located comprises:

calculating a conversion matrix $R_{trans}$ between the first coordinate system and the second coordinate system;

calculating the initial position coordinates of the part to be examined in the second coordinate system where the ultrasound scanning device is located by using a formula $p_1=R_{trans} \, p_0+p_{trans}$ according to the conversion matrix $R_{trans}$;

Wherein $p_1$ represents an initial position vector of the part to be examined in the second coordinate system, $R_{trans}$ represents the conversion matrix between the first coordinate system and the second coordinate system, $p_0$ represents an initial position vector of the part to be examined in the first coordinate system, and $p_{trans}$ represents a position vector of an origin of the first coordinate system relative to the second coordinate system.

4. The ultrasound scanning control method of claim 2, wherein the method further comprises:
controlling a pressure value between the probe and the part to be examined to be a constant value, comprising:
sensing an actual pressure value between the probe and the part to be examined in each control cycle using the force sensor;
calculating a position change amount $\Delta p$ of position change using a preset position change formula according to the actual pressure value, wherein $\Delta p = K_p * e_f + K_d * \Delta e_f$;
Wherein $K_p$ represents a preset proportional value and $K_d$ represents a preset differential gain; $e_f$ represents a pressure error value between a preset target pressure value and the actual pressure value in a control cycle; $\Delta e_f$ represents an amount of error change between a pressure error value corresponding to a current control cycle and a pressure error value corresponding to a previous control cycle; and
controlling the mechanical arm to drive the probe to make a position change with the position change amount $\Delta p$ in a vertical direction based on the second coordinate system.

5. The ultrasound scanning control method of claim 4, wherein the controlling the mechanical arm to drive the probe to make the position change with the position change amount $\Delta p$ in the vertical direction based on the second coordinate system comprises:
controlling the mechanical arm to drive the probe to move downward in the vertical direction based on the second coordinate system, when the position change amount $\Delta p$ is a positive value;
controlling the mechanical arm to drive the probe to move upward in the vertical direction based on the second coordinate system, when the position change amount $\Delta p$ is a negative value; and
not controlling the mechanical arm to drive the probe to move in the vertical direction based on the second coordinate system, when the position change amount $\Delta p$ is 0.

6. The ultrasound scanning control method of claim 1, wherein when the calculated position change amount S is less than or equal to the maximum position change amount, the preset distance is equal to the calculated position change amount S; when the calculated position change amount S is greater than the maximum position change amount, the preset distance is equal to the maximum position change amount.

7. The ultrasound scanning control method of claim 1, wherein the controlling the mechanical arm to drive the probe to move the preset distance along the direction of the lateral impact force comprises:
calculating a moving speed according to a preset control cycle and the preset distance; and
controlling the mechanical arm to drive the probe to move the preset distance along the direction of the lateral impact force at the moving speed.

8. The ultrasound scanning control method of claim 1, further comprising:
determining a center of a smallest circumscribed circle of the target area;
calculating position coordinates of the determined center in the ultrasound image;
determining that the position of the target area in the ultrasound image belongs to the predetermined position, when an abscissa and an ordinate corresponding to the determined center are the same as those corresponding to a center position of the ultrasound image, or when a difference value between the abscissa corresponding to the determined center and the abscissa corresponding to the center position of the ultrasound image is less than a preset value and a difference value between the ordinate corresponding to the determined center and the ordinate corresponding to the center position of the ultrasound image is less than the preset value; and
determining that the position of the target area in the ultrasound image does not belong to the predetermined position, when the difference value between the abscissa corresponding to the determined center and the abscissa corresponding to the center position of the ultrasound image is greater than or equal to the preset value and/or the difference value between the ordinate corresponding to the determined center and the ordinate corresponding to the center position of the ultrasound image is greater than or equal to the preset value.

9. The ultrasound scanning control method of claim 8, wherein the adjusting the set scanning trajectory comprises:
calculating a first difference value between the abscissa corresponding to the position of the target area in the ultrasound image and the abscissa corresponding to the predetermined position;
calculating a second difference value between the ordinate corresponding to the position of the target area in the ultrasound image and the ordinate corresponding to the predetermined position; and
adjusting the scanning trajectory based on the first difference value and the second difference value.

10. An ultrasound scanning device, comprising:
an execution mechanism comprising a force sensor, a mechanical arm and a probe;
a processor; and
a storage device storing one or more computer programs, which when executed by the processor, cause the processor to: control the mechanical arm to drive the probe to move based on a set scanning trajectory;
control the probe to collect an ultrasound image;
identify a target area from the ultrasound image;
calculate a position of the target area in the ultrasound image, and determine whether the position of the target area in the ultrasound image belongs to a predetermined position;
control the mechanical arm to drive the probe to move based on the set scanning trajectory in response that the position of the target area in the ultrasound image belong to the predetermined position;
adjust the set scanning trajectory in response that the position of the target area in the ultrasound image does not belong to the predetermined position; and control the mechanical arm to drive the probe to move based on the adjusted scanning trajectory;
wherein the processor is further caused to:
sense a lateral impact force F received by the probe using the force sensor;
calculate a position change amount S according to the lateral impact force F received by the probe, wherein the calculated position change amount S=F*K, F represents a magnitude of the lateral impact force, and K is a known coefficient; and control the mechanical arm to drive the probe to move a preset distance along a direction of the lateral impact force, according to a magnitude relationship between the calculated position change amount S and a preset maximum position change amount.

11. A non-volatile storage medium having computer programs stored thereon, when the computer programs are executed by a processor of an ultrasound scanning device which comprising an execution mechanism, the processor is configured to perform an ultrasound scanning control method, the execution mechanism comprising a force sensor, a mechanical arm and a probe, wherein the method comprises:

controlling the mechanical arm to drive the probe to move based on a set scanning trajectory;
controlling the probe to collect an ultrasound image;
identifying a target area from the ultrasound image;
calculating a position of the target area in the ultrasound image, and determining whether the position of the target area in the ultrasound image belongs to a predetermined position;
controlling the mechanical arm to drive the probe to move based on the set scanning trajectory in response that the position of the target area in the ultrasound image belong to the predetermined position;
adjusting the set scanning trajectory in response that the position of the target area in the ultrasound image does not belong to the predetermined position; and controlling the mechanical arm to drive the probe to move based on the adjusted scanning trajectory;
wherein the method further comprises:
sensing a lateral impact force F received by the probe using the force sensor;
calculating a position change amount S according to the lateral impact force F received by the probe, wherein the calculated position change amount S=F*K, F represents a magnitude of the lateral impact force, and K is a known coefficient; and
controlling the mechanical arm to drive the probe to move a preset distance along a direction of the lateral impact force, according to a magnitude relationship between the calculated position change amount S and a preset maximum position change amount.

12. The ultrasound scanning device of claim 10, wherein before controlling the mechanical arm to drive the probe to move based on the set scanning trajectory, the processor is further caused to:

determine a part to be examined, and convert initial position coordinates of the part to be examined in a first coordinate system where a hospital bed is located into initial position coordinates of the part to be examined in a second coordinate system where the ultrasound scanning device is located; and
generate the set scanning trajectory based on the initial position coordinates of the part to be examined in the second coordinate system, wherein the set scanning trajectory comprises a plurality of position coordinates.

13. The ultrasound scanning device of claim 12, wherein the converting initial position coordinates of the part to be examined in the first coordinate system where the hospital bed is located into initial position coordinates of the part to be examined in the second coordinate system where the ultrasound scanning device is located comprises:

calculating a conversion matrix $R_{trans}$ between the first coordinate system and the second coordinate system;
calculating the initial position coordinates of the part to be examined in the second coordinate system where the ultrasound scanning device is located by using a formula $p_1 = R_{trans} \, p_0 + p_{trans}$ according to the conversion matrix $R_{trans}$;
wherein $p_1$ represents an initial position vector of the part to be examined in the second coordinate system, $R_{trans}$ represents the conversion matrix between the first coordinate system and the second coordinate system, $p_0$ represents an initial position vector of the part to be examined in the first coordinate system, and $p_{trans}$ represents a position vector of an origin of the first coordinate system relative to the second coordinate system.

14. The ultrasound scanning device of claim 12, wherein the processor is further caused to:

control a pressure value between the probe and the part to be examined to be a constant value, comprising:
sensing an actual pressure value between the probe and the part to be examined in each control cycle using the force sensor;
calculating a position change amount $\Delta p$ of position change using a preset position change formula according to the actual pressure value, wherein $\Delta p = K_p * e_f + K_d * \Delta e_f$;
Wherein $K_p$ represents a preset proportional value and $K_d$ represents a preset differential gain; $e_f$ represents a pressure error value between a preset target pressure value and the actual pressure value in a control cycle; $\Delta e_f$ represents an amount of error change between a pressure error value corresponding to a current control cycle and a pressure error value corresponding to a previous control cycle; and
controlling the mechanical arm to drive the probe to make a position change with the position change amount $\Delta p$ in a vertical direction based on the second coordinate system.

15. The ultrasound scanning device of claim 14, wherein the controlling the mechanical arm to drive the probe to make the position change with the position change amount $\Delta p$ in the vertical direction based on the second coordinate system comprises:

controlling the mechanical arm to drive the probe to move downward in the vertical direction based on the second coordinate system, when the position change amount $\Delta p$ is a positive value;
controlling the mechanical arm to drive the probe to move upward in the vertical direction based on the second coordinate system, when the position change amount $\Delta p$ is a negative value; and
not controlling the mechanical arm to drive the probe to move in the vertical direction based on the second coordinate system, when the position change amount $\Delta p$ is 0.

16. The ultrasound scanning device of claim 10, wherein when the calculated position change amount S is less than or equal to the maximum position change amount, the preset distance is equal to the calculated position change amount S; when the calculated position change amount S is greater than the maximum position change amount, the preset distance is equal to the maximum position change amount.

17. The ultrasound scanning device of claim 10, wherein the controlling the mechanical arm to drive the probe to move the preset distance along the direction of the lateral impact force comprises:

calculating a moving speed according to a preset control cycle and the preset distance; and controlling the mechanical arm to drive the probe to move the preset distance along the direction of the lateral impact force at the moving speed.

18. The ultrasound scanning device of claim 10, wherein the processor is further caused to:
   determine a center of a smallest circumscribed circle of the target area;
   calculate position coordinates of the determined center in the ultrasound image;
   determine that the position of the target area in the ultrasound image belongs to the predetermined position, when an abscissa and an ordinate corresponding to the determined center are the same as those corresponding to a center position of the ultrasound image, or when a difference value between the abscissa corresponding to the determined center and the abscissa corresponding to the center position of the ultrasound image is less than a preset value and a difference value between the ordinate corresponding to the determined center and the ordinate corresponding to the center position of the ultrasound image is less than the preset value; and
   determine that the position of the target area in the ultrasound image does not belong to the predetermined position, when the difference value between the abscissa corresponding to the determined center and the abscissa corresponding to the center position of the ultrasound image is greater than or equal to the preset value and/or the difference value between the ordinate corresponding to the determined center and the ordinate corresponding to the center position of the ultrasound image is greater than or equal to the preset value.

* * * * *